(12) United States Patent
Herdrich et al.

(10) Patent No.: US 8,801,717 B2
(45) Date of Patent: Aug. 12, 2014

(54) SURGICAL GUIDING DEVICE FOR RECONSTRUCTION OF ANTERIOR CRUCIATE LIGAMENT

(75) Inventors: Christoph Herdrich, Wyhl am Kaiserstuhl (DE); Peter Berg, Kraichtal (DE); Eberhard Körner, Knittlingen (DE); Dirk Göthel, Kürnbach (DE); Rainer Siebold, Walldorf (DE)

(73) Assignee: Richard Wolf GmbH, Knittlingen (DE)

( * ) Notice: Subject to any disclaimer, the term of this patent is extended or adjusted under 35 U.S.C. 154(b) by 0 days.

(21) Appl. No.: 13/162,100

(22) Filed: Jun. 16, 2011

(65) Prior Publication Data

US 2011/0313478 A1  Dec. 22, 2011

(30) Foreign Application Priority Data

Jun. 18, 2010  (DE) .......................... 10 2010 024 259

(51) Int. Cl.
  *A61F 2/46* (2006.01)
  *A61B 17/58* (2006.01)
(52) U.S. Cl.
  USPC .......................................... 606/86 R; 606/88
(58) Field of Classification Search
  USPC ................. 606/86 R, 87–89, 96–98
  See application file for complete search history.

(56) References Cited

U.S. PATENT DOCUMENTS

| | | | |
|---|---|---|---|
| 4,781,182 A | 11/1988 | Purnell et al. | |
| 5,350,383 A * | 9/1994 | Schmieding et al. | 606/96 |
| 5,458,602 A * | 10/1995 | Goble et al. | 606/96 |
| 5,643,273 A * | 7/1997 | Clark | 606/96 |
| 5,968,050 A * | 10/1999 | Torrie | 606/87 |
| 6,120,511 A * | 9/2000 | Chan | 606/96 |
| 6,254,606 B1 * | 7/2001 | Carney et al. | 606/102 |
| 6,342,056 B1 * | 1/2002 | Mac-Thiong et al. | 606/96 |
| 6,918,916 B2 | 7/2005 | Gobel et al. | |
| 7,615,743 B2 | 11/2009 | Baykut et al. | |
| 7,842,042 B2 * | 11/2010 | Reay-Young et al. | 606/96 |

FOREIGN PATENT DOCUMENTS

| | | |
|---|---|---|
| DE | 101 46 452 A1 | 4/2003 |
| DE | 10 2007 047 075 A1 | 4/2009 |
| EP | 1 917 921 A2 | 5/2008 |
| WO | 2006125009 A2 | 11/2006 |

OTHER PUBLICATIONS

Office Action Issued Dec. 23, 2010 in German Appln. Ser. No. 10 2010 024 259.4.

* cited by examiner

*Primary Examiner* — Anu Ramana
*Assistant Examiner* — Micahel Araj
(74) *Attorney, Agent, or Firm* — Panitch Schwarze Bellisario & Nadel LLP

(57) ABSTRACT

A surgical guiding device is provided for reconstruction of the anterior cruciate ligament, including a guide arm and a guide hook extending away from the arm. The guide arm is constructed in the form of an arc, supports a mounting that is slidable on the guide arm and has a fixing device for an alignment wire that is separate from the mounting.

10 Claims, 2 Drawing Sheets

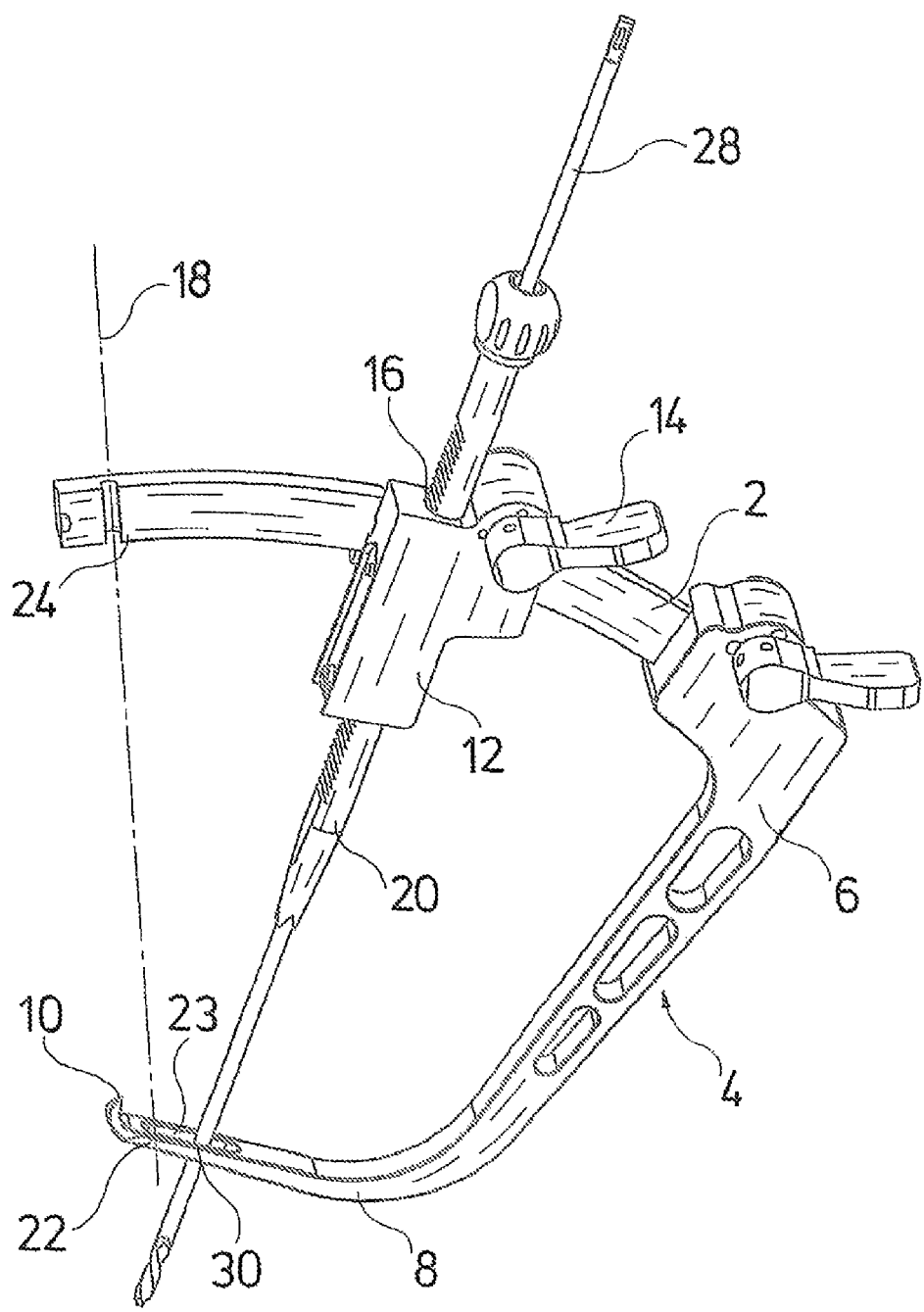

SURGICAL GUIDING DEVICE FOR RECONSTRUCTION OF ANTERIOR CRUCIATE LIGAMENT

BACKGROUND OF THE INVENTION

The invention relates to a surgical guiding device for reconstruction of the anterior cruciate ligament.

Guiding devices for reconstruction of the anterior cruciate ligament are generally used for positioning and/or aligning drilling channels into a bone, these channels being essential to enable anterior cruciate ligament transplants to be inserted. Depending on the surgical method (single-bundle or double-bundle reconstruction), one or two of these drilling channels are created in the bone. To create these drillholes, first the alignment wires are inserted in the bone with the aid of the guiding device. These are then used later in the operation to guide cannulated drills used to open out the drilling channels to a wider diameter, that is, to the diameter of the anterior cruciate ligament transplants that will subsequently be inserted.

A guiding device for single-bundle reconstruction is known from German published patent application DE 101 46 452 A1. This instrument has a guide arm with a permanently fixed mounting for a drill. A guide hook extends away from the guide arm in arched manner, such that the distal end of the hook is facing away from the guide arm and is opposite the mounting for the drill. In this way, the distal end of the guide hook is able to encircle the bone that is to be drilled so that the drill's exit point from the bone may be marked. However, it is only possible to make one targeted drillhole in the bone using these guiding devices, so the instrument is not suitable for use in double-bundle reconstruction.

A similar guiding device, which is suitable for double-bundle reconstruction, is known from German published patent application DE 10 2007 057 075 A1. On this instrument, two openings are provided in the guide hook. A first alignment wire is passed through the first opening to create a first drillhole. Then, the alignment wire is removed from the first opening and mounted in the second opening to position the guide hook correctly for creating the second drillhole. The drawback with this guiding device is that the bone bridge between the two drillholes to be created cannot be defined and adjusted precisely, particularly if the implants are of different diameters.

International patent application publication WO 2006/125009 A2 discloses a further guiding device that is suitable for double-bundle reconstruction. This guiding device has two mountings on the guide arm for two drills or alignment wires, which can be positioned very flexibly with respect to one another and on the guide arm of the guide hook. However, the many adjustment options require a complex construction and manipulating this instrument is complicated. A similar guiding device is known from European patent application publication EP 1 917 921 A2.

BRIEF SUMMARY OF THE INVENTION

In view of this state of the prior art, objects of the present invention are a surgical guiding device for reconstruction of the anterior cruciate ligament that is suitable for double-bundle reconstruction, has a simple construction and is easy to manipulate, but at the same time enables a defined bone bridge to be created between the drillholes that are to be made.

This objects are achieved with a surgical guiding device for reconstruction of the anterior cruciate ligament, including a guide arm and a guide hook extending away from the arm, wherein the guide arm is constructed in the form of an arc, supports a mounting slidable on the guide arm, and has a fixing device for an alignment wire that is separate from the mounting. Preferred embodiments will be evident from the description below and the attached figures.

Like the known guiding devices, the surgical guiding device according to the invention for anterior cruciate ligament reconstruction has a guide arm with a guide hook that extends away from it. The guide hook may be permanently or detachably attached to the guide arm. In particular, it is also possible for the guide hook to be arranged on the guide arm, so as to be slidable in lengthwise direction thereon.

The guide hook has a first section that is adjacent to the guide arm and extends essentially perpendicularly thereto, that is, it extends away from the guide arm essentially normally to the longitudinal axis thereof. If the guide arm is curved, this first section of the guide hook thus extends radially inwardly. A second section of the guide hook extends from the first section on the end farthest from guide arm, and this second section is angled with respect to the first section. The distal end of this second section, that is, the end farthest from the first section, forms the distal end of the guide hook. This distal end is thus at a distance from the first section of the guide hook and is essentially facing the guide arm at a distance therefrom. The distal end of the guide hook is preferably conformed in known manner as a point or blade, which serves to ensure that it can be positioned or fixed securely on the bone.

In order to make the drillholes in the bone, the bone, particularly the tibia, is clasped with the guide hook in such manner that the distal end of the guide hook defines the exit point of the drillhole to be made. After the guide hook has been set, a drilling tool may then be guided via a mounting on the guide arm of the guiding device, such that a straight drillhole is created through the bone to the marked guide point. As was described in the preceding, in order to make the drillhole, an alignment wire is usually set first, to mark the direction of the drillhole in the bone. Afterwards, a cannulated drill is guided along this alignment wire and used to drill a tunnel of the desired diameter in the bone.

According to an embodiment of the present invention, the guide arm of the device is constructed in the form of an arc and a slidable mounting is arranged on the guide arm. This mounting serves to guide the alignment wire or a drill for setting the drillhole. The mounting is constructed and arranged on the guide arm in such manner that it defines a straight direction or axis toward the distal end of the guide hook, so that a drillhole or alignment wire may be inserted in the bone in such a way that it exits the bone at a point defined by the guide hook.

According to an embodiment of the invention, in addition to the mounting, a separate fixing device for an alignment wire is conformed on the mounting. This design makes it very easy to create two drillholes or drilling channels for double-bundle reconstruction. Thus, the mounting may first be slid to a first position on the guide arm, which corresponds to the position of the fixing device. In this position the mounting guides a first alignment wire, so that the wire may be set in defined manner into the bone. Then, this alignment wire is fixed in the set position via the fixing device on the guide arm.

The fixing device is thus designed for fixing the alignment wire in such manner that the alignment wire may particularly be retained on the guide arm in such manner that is not movable relative thereto in the direction of the guide arm. When the alignment wire is retained securely on the fixing device, the mounting may then be moved to a second position to create the second drillhole and to set a second alignment wire. Since the first alignment wire is held securely in place by the fixing device at the same time, this makes it easy to insert the second alignment wire at a defined distance and angle relative to the first alignment wire, along which the two drillholes will be made subsequently.

In order to be able to set the first drillhole by inserting an alignment wire, the mounting on the guide arm is preferably arranged slidably on the guide arm as described, in such manner that it is movable or slidable in the lengthwise direction of the guide arm to a first position, which corresponds to the positions of the fixing device. As a result, after the alignment wire has been set, this makes it possible to seat or retain the wire in the fixing device without having to displace it significantly in its position relative to the guide arm.

It is further preferred if an elongated slot is formed in the guide hook at a distance from the guide arm, that is, close to the distal end of the guide hook, of which slot a first part or longitudinal section is aligned with the fixing device on the guide arm to accommodate a first alignment wire. This first part thus essentially defines the exit point for the first drillhole on the guide hook. The mounting is positionable on the arc-shaped guide arm in such manner that it sets a direction or axis for the drillhole to be created or for guiding the alignment wire, this direction or axis essentially extending along the radius of curvature of the arc-shaped guide arm.

Thus, when the mounting is located in the position of the fixing device, the guide axis, which is defined by the mounting, extends essentially radially relative to the guide arm and through the first part of the elongated slot of the guide hook. In this way, a first alignment wire may be inserted in the bone at the position of the fixing device and at the same time guided through the first part of the elongated slot in the guide hook.

The alignment wire may then be retained in this position by the fixing device, and the mounting may be moved to a second position as described for inserting a second alignment wire. The fixing device for holding the first alignment wire lines up with the first part of the elongated slot, so that they both are preferably on a radius of the curved guide arm or an axis in the direction of the radius passes through the fixing device and the first part of the elongated slot. The center point of the curvature of the guide arm is preferably located on the side of the guide hook farthest from the guide arm, that is, outside of the guiding device.

A second part or lengthwise section of the elongated slot is preferably located in the guide hook and farther from the distal end of the guide hook than the first part. The second part also preferably lines up with the mounting on the guide track for setting a second alignment wire, when the mounting is located in at least a second predefined position, which is at a distance from the fixing device in the direction of the curved longitudinal axis of the guide arm. This means that in order to create the second drillhole at a defined position relative to the first drillhole or to a first inserted alignment wire, the mounting is moved in the lengthwise direction of the guide arm away from the position of the fixing device and on the guide arm to the second position. In this position, the mounting defines a second guide axis, which also extends radially relative to the guide arm.

However, the curvature of the guide arm means that this guide axis extends at an angle to the first guide axis, which was defined by the mounting in its first position, that is, at the position of the fixing device. In this way, the mounting in this second position defines a guide axis along which a second alignment wire is inserted, in such manner that it extends through the bone at an angle to the first alignment wire. In this case, the second guide axis extends through the second part of the elongated slot in the guide hook so that the second alignment wire passes through this second part. In this context, the mounting is positioned on the guide arm such that a defined bone bridge is created between the two drillholes on the exit side of the bone.

In this respect, it is preferred if there are multiple second positions, in which the mounting, or the guide axis defined by the mounting, lines up with the second part of the elongated slot in the guide hook. In order to make this possible over a larger adjustment range of the mounting along the guide arm, the hole is preferably conformed as an elongated hole extending for a significant distance in the longitudinal direction of the guide hook. The extension direction of the elongated slot is thus preferably in the same plane as the longitudinal direction of the guide arm.

Instead of furnishing an elongated slot, it is also conceivable to form two holes arranged at a distance from one another in the guide hook, wherein a second hole, which corresponds to the second part of the elongated slot described above, preferably also has the form of an elongated slot, to enable the alignment wire for the second drillhole to be guided for multiple second positions of the mounting also.

The fixing device is particularly preferably constructed as an open groove extending in the direction of the guide arm's radius of curvature. In this case, the whole length of the groove is open to a lateral surface of the guide arm, so that an alignment wire may be inserted in the groove from the side. The longitudinal axis of the groove extends in the direction of the radius of curvature and thus in the direction of the first guide axis, which is defined by the mounting when the mounting is at the position of the fixing device. It thus becomes possible to hold an alignment wire, which has been inserted in the bone with the mounting in the first position, in this position via the fixing device. For this, the alignment wire only needs to be shifted transversely to the longitudinal direction of the groove to place it in the groove.

To enable this, the mounting also preferably has a slot extending in the longitudinal direction of the mounting and is movable on the guide arm to a first position in which the slot is located opposite the groove that forms the fixing device. When the slot and the groove are opposite one another, it is possible to push an alignment wire from the mounting, through the slot and into the groove of the fixing device, so that it is then held in place by the fixing device and the mounting may be moved into the second position described above at a distance from the fixing device. When the alignment wire is moved from the mounting into the groove of the fixing device, a movement essentially perpendicular to the extension direction of the guide arm or the longitudinal axis of the guide arm is made, so that the alignment wire is not displaced in its angular location along the guide arm.

According to a further preferred embodiment of the invention, a first axis, which extends through the first part of the elongated slot in the guide hook and the fixing device on the guide arm, and a second axis, which extends through the second part of the elongated slot in the guide hook and the mounting, intersect at a fixed point for at least one and preferably several possible positions of the mounting, which fixed point is located on a side of the guide hook facing away from the guide arm and outside the guiding device. This point is more preferably the center of curvature of the guide arm. This design enables the guide axes defined by the mounting always to pass through a predetermined, fixed intersection point, particularly the center of curvature of the guide arm, preferably for all possible positions of the mounting along the guide arm. This ensures that the axes along which the two alignment wires are inserted into the bone always intersect at a fixed, predetermined point, which is located outside the guiding device and outside the bone. The angle between these axes may be larger or smaller depending on the diameter of the drillholes to be created, so that the width of the bone bridge is defined on the exit side of the drillholes in the bone.

In particular, this enables the predetermined width of the bone to be maintained easily at all times, even for different drillhole diameters. The width of this bone bridge may be defined in advance by sliding the mounting along the guide arm relative to the position of the fixing device. With larger drillhole diameters, the mounting is moved correspondingly farther away from the fixing device, so that the angle between the axes, along which the alignment wires are introduced into the bone, becomes larger. This also has the effect of increasing the distance between the center axes of the drillholes on the exit side of the bone, so that the distance between the outer sides of the drillholes, that is, the width of the bone bridge, may be kept constant.

In order to make it easier for the surgeon to position the mounting correspondingly, markings may be applied to the guide arm, indicating predetermined positions for the mounting at a distance from the fixing device. Thus, at least one second predetermined position for the mounting is characterized with a marking preferably at a distance from the fixing device on the guide arm, wherein the marking is positioned such that a predetermined width of the bone bridge is maintained between the drillholes when a first drillhole is inserted at the position of the fixing device and a second drillhole at the position of the marking taking into account the drillhole diameter. This makes it considerably easier to drill the holes.

After the guide hook is set, initially a first alignment wire is introduced into the bone via the mounting when the mounting is at the position of the fixing device. The wire is then fixed on the fixing device and the mounting is moved to the position of the marking on the guide arm. Then, a second alignment wire is inserted in the bone through the mounting. In this case, the preset marking ensures that the alignment wires are guided through the bone at exactly the desired angle and distance, so that when the drillholes have been completely formed with a given hole diameter, a bone bridge of predetermined width may be maintained.

Multiple markings are preferably conformed on the guide arm, and are associated with different hole diameters, so that the surgeon is very easily able to place the mounting at the correct mounting location depending on the diameter of the drillholes to be made. Thus, multiple markings are preferably provided and are located on the guide arm, such that a sum of the hole diameters from the first and second drillholes is associated with each marking, so that the predetermined bone bridge width is maintained when the drillholes are created with these two diameters by positioning the mounting on the marking that corresponds to the sum of the two selected hole diameters.

When the distance and angle between the alignment wires is defined, the only significant determining value for the bone bridge width is the sum of the hole diameters. To this extent, it preferably provided to include markings for various sums of the two hole diameters on the guide arm at the respective required position for the mounting. In this way, the surgeon only has to add the diameters of the holes he intends to drill, and he can then move the mounting to a marking corresponding to the respective sum in order to be able to insert the second alignment wire into the bone at exactly the correct distance and angle with respect to the first alignment wire. This means, certain angles and distances between the two guide axes, along which the alignment wires are inserted into the bone, are associated with certain hole diameter sums and are marked accordingly on the guide arm. In this way, it is very easily possible always to maintain the same, constant bone bridge width even with different hole diameters.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings:

FIG. 2 is a perspective view of the guiding device of FIG. 1 seen from the rear, in which the mounting is located in a second position.

DETAILED DESCRIPTION OF THE INVENTION

Figure 1:
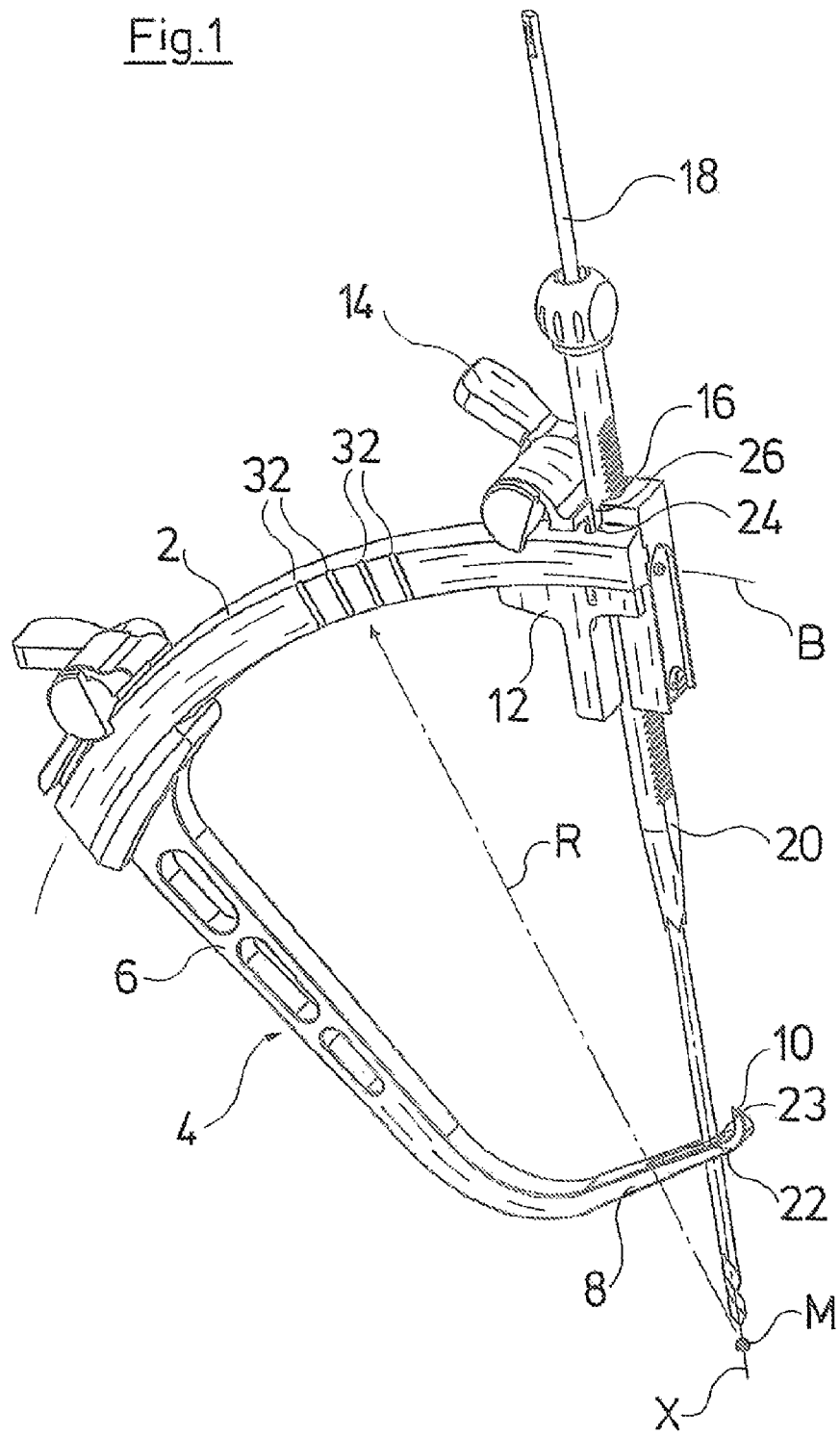
FIG. 1 is a perspective view of a guiding device according to an embodiment of the invention, in which the mounting is located in a first position.

The guiding device according to the invention shown in the figures has an arc-shaped guide arm 2. This is curved in the form of an arc having radius R about point M. A guide hook 4 is attached, in this case detachably, to one extremity of guide arm 2. Guide hook 4 has a first section 6 that extends outwardly from guide arm 2. This section extends perpendicularly to the longitudinal direction, that is, perpendicularly to the arc described by guide arm 2. A second section 8 is connected to first section 6 and at an angle thereto, the distal end of which second section forms the distal end of guide hook 4, which is constructed as a tip 10 facing toward guide arm 2. Second section 8 of guide hook 4 is angled in a known manner, such that it is able to encircle the bone in which the holes are to be drilled, so that tip 10 may be positioned on the rear of the bone at that point where the drillholes to be created exit the bone. In this way, it is possible to mark the exit sites of the drillholes to be created with the guide hook, and particularly with the distal end thereof, and to position the guiding device correspondingly on the bone.

A mounting 12 is also arranged on guide arm 2. Mounting 12 is displaceable on guide arm 2 in the longitudinal direction thereof, that is to say along arc B defined by guide arm 2. In order to be able to fix mounting 12 in a desired position, a clamping lever 14 is provided, which may be rotated to fix mounting 12 in its position on guide arm 2 with clamps. Mounting 12 is also constructed such that it may be easily removed laterally from guide arm 2, that is, it defines a laterally open groove into which guide arm 2 is inserted.

Mounting 12 has a guide 16 that defines a guide axis X, along which an alignment wire 18 may be inserted into the bone. A bushing 20 is arranged in guide 16, so as to be displaceable in the direction of guide axis X, and through which alignment wire 18 is threaded. In order to insert first alignment wire 18 into the bone, guide hook 4 is positioned with tip 10 on the rear of the bone in such manner that a first part or section 22 of an elongated slot 23 close to the distal end of guide hook 4 is located opposite the desired exit site of the intended drillhole. Then, bushing 20 is slid forward, so that the distal end thereof is positioned over the desired entry site for the drillhole. In this way, the bone is clamped between the distal end of bushing 20 and tip 10. Then, alignment wire 18 is inserted into the bone, passed through the bone so that it exits at the rear of the bone, and is guided through part 22 of elongated slot 23 in guide hook 4.

Then, bushing 20 may be removed from mounting 12 in the proximal direction, and first alignment wire 18 that is inserted in this way may be displaced laterally from 16, that is, perpendicularly to longitudinal axis B, and into a fixing device 24. Fixing device 24 is constructed as a groove in guide arm 2, and this groove extends over the entire width of guide arm 2 in the direction of first guide axis X, that is, essentially radially relative to guide arm 2. In order to be able to move alignment wire 18 out of guide 16 and into fixing device 24, guide 16 is furnished with a lateral slot 26, that is, on the side thereof facing guide arm 2, which slot extends over the entire length of the guide and through which alignment wire 18 is movable perpendicularly to its direction of extension out of mounting 12 and into the facing groove of fixing device 24. This is done when mounting 12 is located in its first position, which corresponds to the position of fixing device 24. Then, first alignment wire 18 is retained securely in fixing device 24, as indicated by the longitudinal axis of alignment wire 18 shown in FIG. 2.

In order to insert a second alignment wire in the bone, mounting 12 is then slidable long longitudinal axis B of guide arm 2. Then, the guiding device is retained securely in the defined position on the bone by first alignment wire 18. In the second position, as shown in FIG. 2, mounting 12 is located at a distance along longitudinal axis B from fixing device 24, and the second guide axis, which is now defined by guide 16 in mounting 12, in turn extends radially with respect to arc-shaped guide arm 2, so that the second guide axis always intersects the first guide axis, which is defined by first alignment wire 18, at fixed point M, which is located outside the guiding device, that is, on the side of guide hook 4 farthest from guide arm 2.

In this position, bushing 20 is set on the bone again, and a second alignment wire 28 is inserted into the bone. Then, at the exit site alignment wire 28 extends through a second part or section 30 of elongated slot 23 in guide hook 4. Second section 30 of elongated slot 23 is located farther from the distal end, that is, tip 10. In this way, second alignment wire 28 is able to be inserted into the bone at a defined angle relative to first alignment wire 18. Then, the actual drillholes may be formed in known manner along alignment wires 18 and 28, the alignment wires being used to guide the drill.

In order achieve a defined width of the bone bridge at the exit site of the drillhole, markings 32 are provided on guide arm 2, and these indicate the predetermined positions for placing mounting 12 on guide arm 2. This provides a simple method of positioning mounting 12 for inserting second alignment wire 28, merely by sliding mounting 12 to a given marking 32 and fixing it on guide arm 2 with clamps. Markings 32 take into account the diameters of the drillholes that will be created later, ensuring thereby that the width of the bone bridge at the exit site will remain constant even for different hole diameters.

The larger the sum of the diameters of the two drillholes to be made, the greater must be the distance between the longitudinal axes of alignment wires 18 and 28 and the larger the angle must be between alignment wires 18 and 28. For this reason, multiple markings 32 are provided on guide arm 2, each marking being allocated to a given sum of the hole diameters. Thus, only the diameters of the planned drillholes would need to be added in order to be able to position second alignment wire 28, and mounting 12 would have to be slid along guide arm 2 to the marking 32 that corresponds to this sum. Then, second alignment wire 28 is inserted into the bone in this position, it being assured that alignment wires 18 and 28 are at such an angle and distance relative to one another that a bone bridge of defined width will be created after the drilled holes have been shaped as required.

The guide axes defined by mounting 12 and guide 16 intersect at fixed point M regardless of the position of mounting 12 along guide arm 2, since these guide axes extend in the direction of the radius. In FIG. 1 radius R is illustrated for exemplary purposes at one of the markings 32. This means that if second alignment wire 28 were set on this marking 32, it would extend along illustrated radius R and intersect with first alignment wire 18 at point M, outside of the guidance device and outside of the bone.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A surgical guiding device for reconstruction of the anterior cruciate ligament, comprising a guide arm (2), a guide hook (4) extending away from the guide arm, wherein the guide arm (2) has an arc form, a mounting (12) supported by and slidable on the guide arm (2), and a fixing groove (24) in the guide arm for an alignment wire (18, 28), wherein the fixing groove is separate from the mounting (12),
    wherein the mounting (12) is slidably arranged on the guide arm (2) in such manner that the mounting (12) is movable in a longitudinal direction of the arc (B) of the guide arm (2) to a first position that corresponds to the position of the fixing groove (24).

2. The surgical guiding device as recited in claim 1, further comprising an elongated slot (23) formed in the guide hook (4) at a distance from the guide arm (2), wherein a first part (22) of the elongated slot lines up with the fixing groove (24) in the guide arm (2) to accommodate a first alignment wire (18).

3. The surgical guiding device as recited in claim 2, wherein a second part (30) of the elongated slot (23) lines up with the mounting (12) on the guide arm (2) to accommodate a second alignment wire (28) when the mounting (12) is positioned in at least one second predetermined position, which is at a distance from the fixing groove (24) in the longitudinal direction of the arc (B) of the guide arm (2).

4. The surgical guiding device as recited in claim 3, wherein the fixing groove (24) is formed as an open groove having a longitudinal axis extending in a direction of the radius of curvature (R) of the guide arm (2).

5. The surgical guiding device as recited in claim 4, wherein the mounting (12) has a slot (26) extending in a longitudinal direction of the mounting and the mounting (12) is movable on the guide arm (2) to a first position, wherein the slot (26) is opposite the open groove.

6. The surgical guiding device as recited in claim 2, wherein a first axis (X) extending through the first part (22) of the elongated slot (23) in the guide hook (4) and through the fixing groove (24) on the guide arm (2), and a second axis extending through a second part (30) of the elongated slot (23) in the guide hook (4) and through the mounting (12), intersect one another at a fixed point (M) for at least one position of mounting (12), and wherein the fixed point is located on a side of the guide hook (4) facing away from the guide arm (2) and outside the guiding device.

7. The surgical guiding device as recited in claim 1, wherein at least one second predetermined position is identified for mounting (12) with a marking (32) on the guide arm (2) and at a distance from a position of the fixing groove (24), and wherein the marking (32) is positioned in such manner that when a first drillhole is created at the position of the fixing device (24) and a second drillhole is created at the position of the marking (32) taking into account the diameter of the drillhole, a predetermined width of a bone bridge is maintained between the drillholes.

8. The surgical guiding device as recited in claim 7, wherein multiple markings (32) are provided, the markings being positioned on the guide arm (2) such that each marking (32) is assigned to a sum of hole diameters from the first and second drillholes, and such that by positioning mounting (12) on one of the markings (32) that corresponds to the sum of the selected hole diameters, the predetermined width of the bone bridge is maintained when the drillholes are created with the corresponding hole diameters.

9. The surgical guiding device as recited in claim 1, wherein the mounting is further movable in the longitudinal direction of the arc (B) of the guide arm to a second position that is spaced-apart from the fixing groove.

10. The surgical guiding device as recited in claim 1, wherein the mounting (12) is configured to guide the alignment wire (18, 28).

\* \* \* \* \*